United States Patent [19]

Johnson et al.

[11] Patent Number: 4,714,168

[45] Date of Patent: Dec. 22, 1987

[54] CONTAINER FOR DISPOSABLE EXPENDED MEDICAL SUPPLIES

[76] Inventors: William G. Johnson, 472 Indian Road, Burlington, Ontario, Canada, L7T 3T3; Gary B. Romagnoli, 41 Allan Drive, St. Catherines, Ontario, Canada, L2N 1G1

[21] Appl. No.: 879,953

[22] Filed: Jun. 30, 1986

[51] Int. Cl.$^4$ .......................... B65D 5/42; B65D 5/46; A61M 5/32

[52] U.S. Cl. ..................... 220/1 T; 206/366; 220/255; 220/315; 220/329; 229/907; 232/47

[58] Field of Search .............. 220/1 T, 255, 315, 329; 206/366, 365; 229/907; 232/47, 43.1, 56, 43.2, 44

[56] References Cited

U.S. PATENT DOCUMENTS

| | | | |
|---|---|---|---|
| 527,799 | 10/1944 | Martin | 232/47 |
| 1,136,050 | 4/1915 | Razny | 232/47 |
| 1,248,584 | 12/1917 | Williams et al. | 232/47 |
| 1,322,522 | 11/1919 | Bixon | 232/47 |
| 3,226,007 | 12/1965 | Thies et al. | 229/39 |
| 4,121,755 | 10/1978 | Meseke et al. | 229/38 |
| 4,315,592 | 2/1982 | Smith | 229/38 |
| 4,488,643 | 12/1984 | Pepper | 206/366 |
| 4,580,688 | 4/1986 | Harris et al. | 206/366 X |

FOREIGN PATENT DOCUMENTS

| | | | |
|---|---|---|---|
| 54239 | 7/1911 | Switzerland | 232/47 |
| 62548 | 10/1912 | Switzerland | 232/47 |

OTHER PUBLICATIONS

Infection Control, 1985, vol. 6, No. 1, "Disposable Needle and Syringe Containers", Steven A. Weinstein.

Primary Examiner—William Price
Attorney, Agent, or Firm—Ridout & Maybee

[57] ABSTRACT

A container for disposable syringes has a body structure defining an interior chamber and a laterally elongated upper opening in an upward and forward surface of the container, the opening having a length and width sufficient to accept expended medical syringes of commonly used sizes broadside on, an upwardly opening lid for covering the opening and connected by a hinge to the rear of the elongated opening for movement upward and away from the opening, a laterally elongated chute extending into the body structure and having a front wall extending downwardly and rearwardly from the opening to a lower opening into the interior chamber, a wall extending downwardly from the hinge of the lid into the chute to form a labyrinth effective to arrest passage of a human hand through the chute short of the lower opening of the latter, and structure to control passage to the rear of the lower end of the front wall of the chute, into the interior chamber, of a syringe dropped down the chute. Preferably the wall is integral with the lid, whilst the control structure to the rear of the opening may be either a downward extension of the wall, or a separate structure. The structure of the container may be readily fabricated from either a cardboard blank, or from plastic or metal.

13 Claims, 5 Drawing Figures

CONTAINER FOR DISPOSABLE EXPENDED MEDICAL SUPPLIES

FIELD OF THE INVENTION

This invention relates to containers for the disposal of expendable medical supplies, especially although not exclusively used disposable syringes.

BACKGROUND OF THE INVENTION

The problems associated with the disposal of such supplies are discussed in an article by Steven A. Weinstein and edited by Sue Crow, published in Infection Control, Volume 6, No. 1, 1985. This article sets out a number of desirable features of containers intended for this purpose, and which are believed to represent current thinking in the field. As far as the requirements set forth for the opening into the container are concerned, it should be emphasized that it is now considered important on the one hand that the opening into the container be easy to use and encourages safe handling of supplies by busy medical personnel, but on the other hand that it presents a substantial resistance to attempts to remove material from the container and that it avoids the presence of contaminated areas on the exterior of the container. These requirements are quite difficult to reconcile, particularly bearing in mind that it is difficult to provide an opening large enough to pass readily a 60 cc disposable syringe, which may be up to 25 cm long if the plunger is extended and may have a width over the finger grips of some 5 cm, whilst preventing hand access to the interior of the container. This problem is aggravated where a relatively compact container is required, as for bedside use (where prevention of patient access is very important), or use on mobile trolleys.

Examples of containers intended for use in receiving expended medical supplies of the type discussed above are to be found in U.S. Pat. No. 3,226,007 issued to Thies et al on Dec. 28, 1965; U.S. Pat. No. 4,121,755 issued to Meseke et al on Oct. 24, 1978; U.S. Pat. No. 4,315,592 issued to Smith on Feb. 16, 1982; and U.S. Pat. No. 4,488,643 issued to Pepper on Dec. 18, 1984. All but the Pepper patent contemplate the use of corrugated cardboard or similar foldable material to provide a container which is cheap to produce and can be knocked down for storage, and all provide some form of restriction of the container opening.

The Thies container provides an arrangement of interacting flaps in the top of the container which form a valve through which syringes may be pushed longitudinally into the interior of the container, and which prevents egress of an item once inserted. Although longitudinal insertion through a multi-flap valve enables the size of the valve opening to be minimized, it falls short of current desiderata in certain respects. Firstly, a user may need to use fingers to push an item right through the valve, and in doing so risks needle stick if the contents reach near the top; a tamperer also faces similar risks. Secondly, the endwise pushing of the syringe produces two problems. If the syringe is inserted needle first, as will normally be the case, the bottom of the container must be able to resist the direct impact of the needle, and residual fluid may be ejected from the syringe on impact. If the syringe is reversed for any reason, the user again risks needle stick. The exterior flap covering the opening is moreover likely to become contaminated during use of the container.

The Meseke container improves upon the Thies container in two respects, in that it permits sideways insertion of syringes and may provide an outer flap to cover the contaminated flap areas prior to removing the container for disposal. The increased size of the valve however means that there is little restriction on hand entry through the flap valve, even though such entry is less necessary during normal usage.

The Smith patent recognizes the importance of allowing materials to be placed in the container without a user risking injury from its existing contents. It thus provides the container with an outer lid containing a first longitudinal opening through which a syringe or similar article may be dropped sideways on, and an internal flap structure defining a ramp beneath the first opening which directs the article through a second longitudinal opening laterally displaced from the first opening, into the interior of the container proper. When the container is to be removed for disposal, the internal flap may be pulled outwardly through a slot so as to pull the ramp upwardly to close the opening in the upper lid. Although the labyrinth provided by the laterally offset outer and inner openings makes hand access more difficult, dimensional limitations make it difficult to provide adequate security in a compact container, and the fact that the edges of the openings are unsupported and cut through a single thickness of cardboard means that it is possible for somebody to force their hand through the openings without too much difficulty. It is also difficult to design the openings so as to allow easy passage of articles without unduly weakening the structure, and the container after use presents external surfaces which may be contaminated.

The Pepper structure provides somewhat similar functionality to the Thies container, but in moulded synthetic plastic and with the addition of a needle bending or breaking device. At one time, it was considered desirable, and in some jurisdictions required, to bend or break the needles of syringes prior to disposal, in order to prevent subsequent misuse. Current thinking is that such bending or breaking during or prior to insertion of a syringe into a disposal container is undesirable, both because of the risk of needle stick injuries, and because of dispersion of fluid material in spray or aerosol form which can take place at the instant of breakage.

SUMMARY OF THE INVENTION

The object of the present invention is to provide containers of the class discussed above, which can be economically and compactly constructed, which are easy to use, and which endeavour to meet the requirements of occupational health, safety and hospital authorities.

According to the invention there is provided a container for disposable syringes comprising a body structure defining an interior chamber and a laterally elongated upper opening in an upward and forward surface of the container, the opening having a length and width sufficient to accept expended medical syringes of commonly used sizes broadside on, an upwardly opening lid for covering the opening and connected by a hinge to the rear of the elongated opening for movement upward and away from the opening, a laterally elongated chute extending into the body structure and having a front wall extending downwardly and rearwardly from the opening to a lower opening into the interior chamber, a wall extending downwardly from the hinge of the lid into the chute to form a labyrinth effective to arrest passage of a human hand through the chute short of the lower opening of the latter, and structure to control passage to the rear of the lower end of the front wall of the chute, into the interior chamber, of a syringe dropped down the chute.

Preferably the wall is integral with the lid, whilst the control structure to the rear of the opening may be either a downward extension of the wall, or a separate structure. The structure of the container may be readily fabricated from either a cardboard blank, or from plastic or metal.

Whilst cardboard blanks provide compact storage, they require to be erected before use, and it may be difficult to provide adequate leak and puncture resistance to meet all test requirements.

Further features of the invention will become apparent from the following description of exemplary preferred embodiments thereof with reference to the accompanying drawings.

SHORT DESCRIPTION OF THE DRAWINGS

In the drawings:

FIG. 5 shows the layout of a blank suitable for erection into a container having the features of FIG. 4.

DESCRIPTION OF THE PREFERRED EMBODIMENTS

Figure 1:
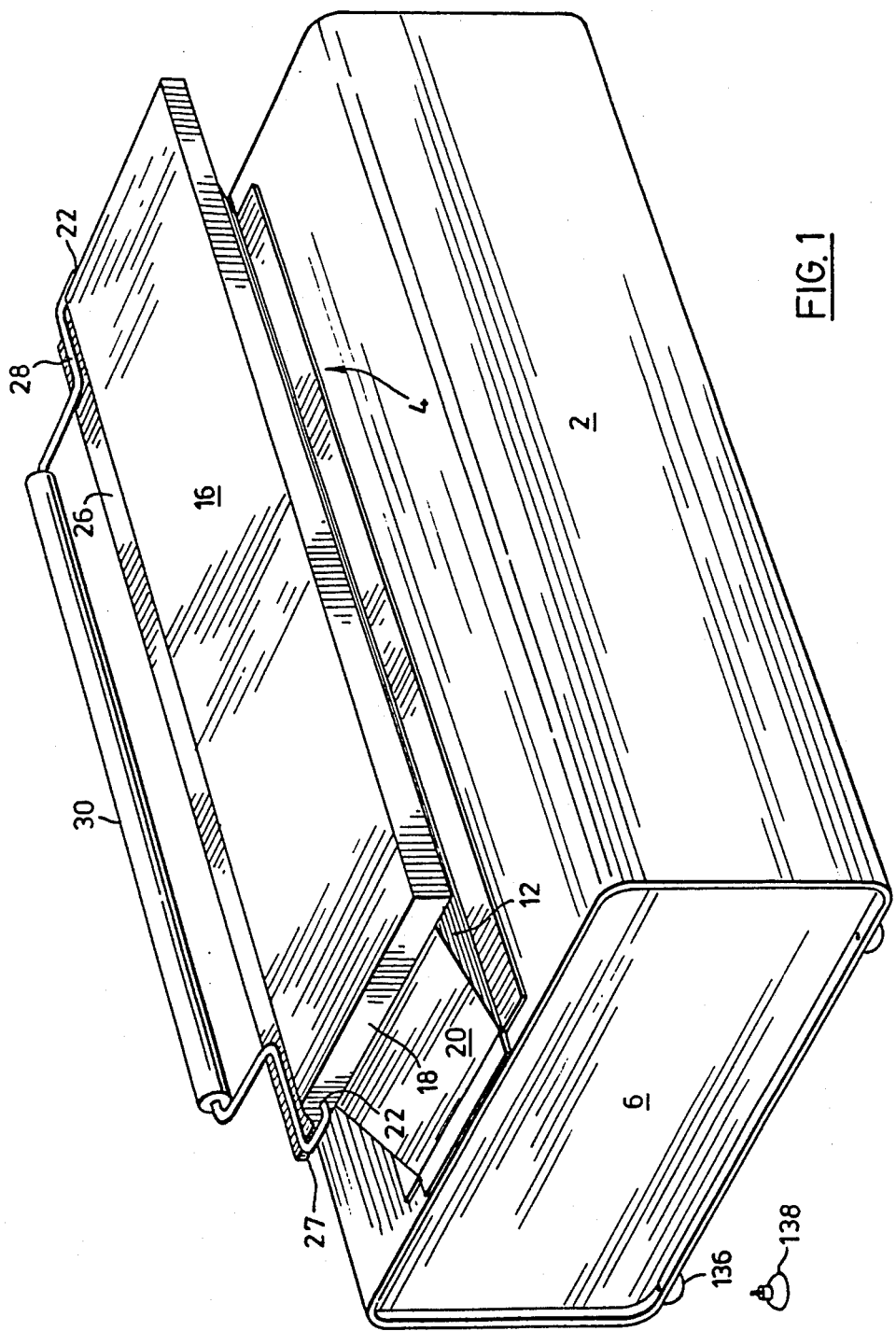
FIG. 1 is a perspective view from in front, one side and above of a first embodiment of the invention suitable for fabrication from metal or plastic.
Figure 2:
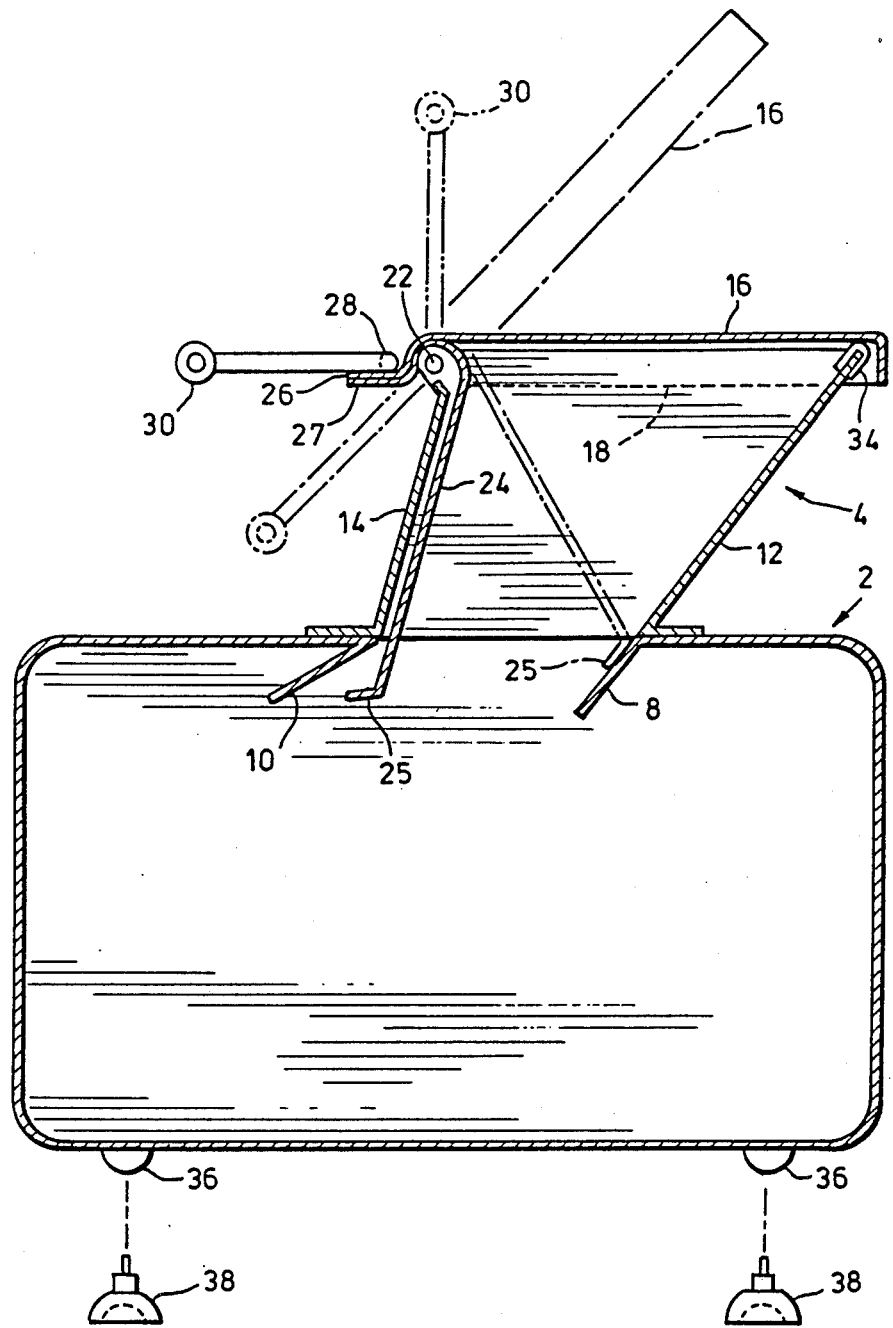
FIG. 2 is a vertical cross section through the container from front to rear.

Referring to FIGS. 1 and 2, the container shown is fabricated from tinplate, although the design can readily be adapted to fabrication from synthetic plastics. The container has a lower main body portion 2 and an upper body portion 4 secured to the top of the main body portion. The main body portion is conveniently a rectangular tinplate can body fabricated from conventional can stock and of the type widely utilized for the sale of liquid products. Conveniently, a can body having a capacity of about 1 gallon will be adequate for many applications, but larger bodies can of course be used. The usual neck for a screw cap may be omitted, the ends 6 of the can being blind, but the upper surface (as seen in the Figures) is formed with an elongated opening about 25 cm by 5 cm. These dimensions are exemplary, with the size of the opening being selected to be a little more than sufficient to allow easy broadside on passage of the largest syringe to be received. This opening may be provided by forming an H shaped cut in the can, and bending inward the flanges 8 and 10 so formed to provide continuations of front and rear walls 12 and 14 of the upper body portion.

The upper body 4 defines a chute with a horizontal top opening at the upper front of the container, and a front wall descending downwardly and rearwardly into the container. The rear wall also extends downwardly into the container, and converges somewhat towards the front wall so as to facilitate placing of articles into the chute. The top opening is closed by a lid 16 having side flanges 18 hinged to side walls 20 of the chute by pivots 22. The lid is associated with a downwardly extending wall 24 which when the lid 16 is closed hangs from the pivots 22 adjacent the rear wall 14 of the chute, with a further downward extension 25 adjacent the flange 10. The lid 16 also has a rearwardly extending flange 26 upon which rests cranked portions 28 of a wire handle 30 connected to the lid, forwardly of the flange 26 by the pivots 22, which are formed by the ends of the wire forming the handle. The wall 24 also has a rearwardly extending flange 27 extending beneath the flange 26 so that opening of the lid will swing the wall 24 forwardly across the centre. The flanges 26 may be either attached or separate, as discussed further below. The handle may be lifted to vertical position as shown in broken lines in FIG. 2 to provide means for carrying the container, but also has a further function described below. In order to maintain the lid 16 normally closed, even if the unit is overturned, a magnet in the form of beading 34 of flexible magnetic material may be applied to the top edge of the wall 12.

The bottom of the body 2 may be equipped or formed with feet 36, which may be further equipped with suction cups to stabilize the unit in counter top locations where no mounting brackets are available. In use, the unit is anchored in a desired location, either in mounting brackets on a wall, unit of furniture or nursing trolley, or by suction cups or other suitable means on a counter top or other flat surface. When it is desired to dispose of a syringe or other item for the disposal of which the unit is intended, downward hand pressure on the handle 30 will overcome the magnet 34 or other detent holding the lid 16 in the closed position, and the latter, together with the wall 24, will then move upwards until the extension 25 contacts the front walls 12 or its extension 8. The wall 24 and extension 25 thus bridge the chute formed by body portion 4 to form a hopper into which the syringe may be dropped broadside on. The lid 16 protects the hand of the user which is holding the lid open from any accidental contact with the syringe or its contents. When the handle 30 is released, the lid 16 will move towards the closed position, and the extension 25 retreats from the syringe in the hopper to allow its controlled discharge from the chute into the main body of the container, thus minimizing the force with which it strikes the bottom of the container and making it unlikely that it will land point first. This, combined with the natural puncture resistance of the tin plate utilized, minimizes the possibility of penetration of the container. Since when the lid 16 is open, the wall 24 blocks the chute formed by the upper body portion 4, it can readily be made impossible, without extreme force, for a hand to be inserted into the main body 2 of the container past both the lid 16 and the wall 24. Likewise, a person inserting material into the container is protected by the wall 24 from material already in the container. The tapered opening of the chute, and the additional guidance provided by the lid 16 make it very easy to insert material. In the event of the container being dropped or knocked over, then even if the lid 16 should open, the inner wall 24 can move to close the chute to avoid danger of spillage of the contents of the container, the body of which is, because of its construction, readily made leakproof. If the flanges 26 and 27 are unconnected, the wall 24 can move to close the chute even if the lid 16 remains open.

In the unit described, the upper and lower body portions are connected by soldered or welded flanges. It would be possible to redesign the parts so that the upper body is a snap fit in the lower body, and the body portions could be moulded from synthetic plastic as a single unit or two units subsequently connected together.

Figure 3:
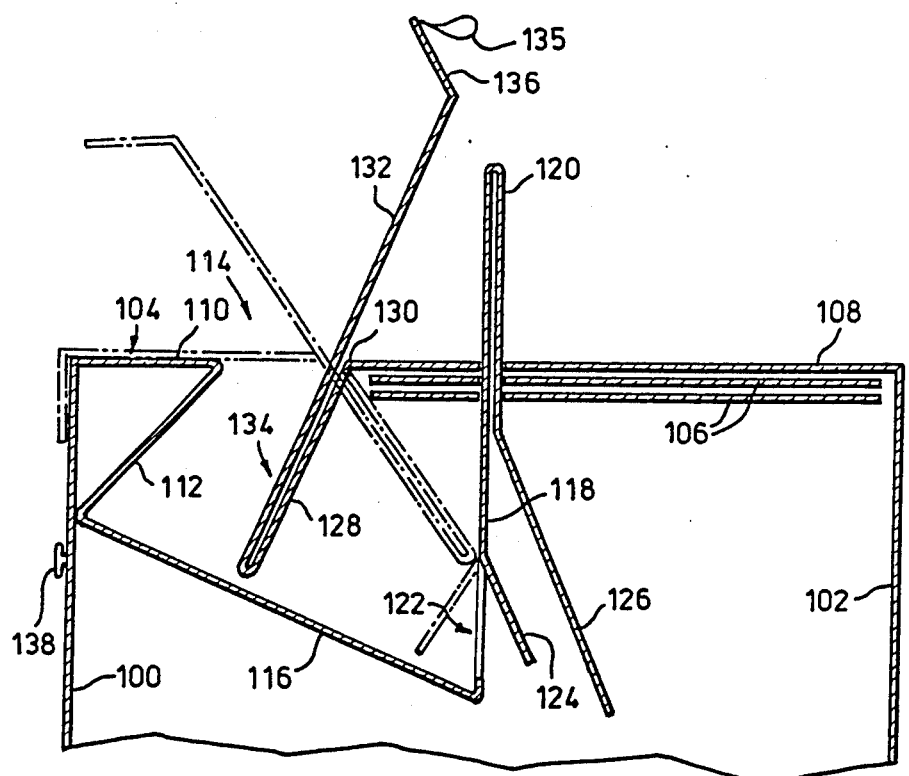
FIG. 3 is a partial cross section through a second embodiment of container, suitable for fabrication from cardboard.
Figure 4:
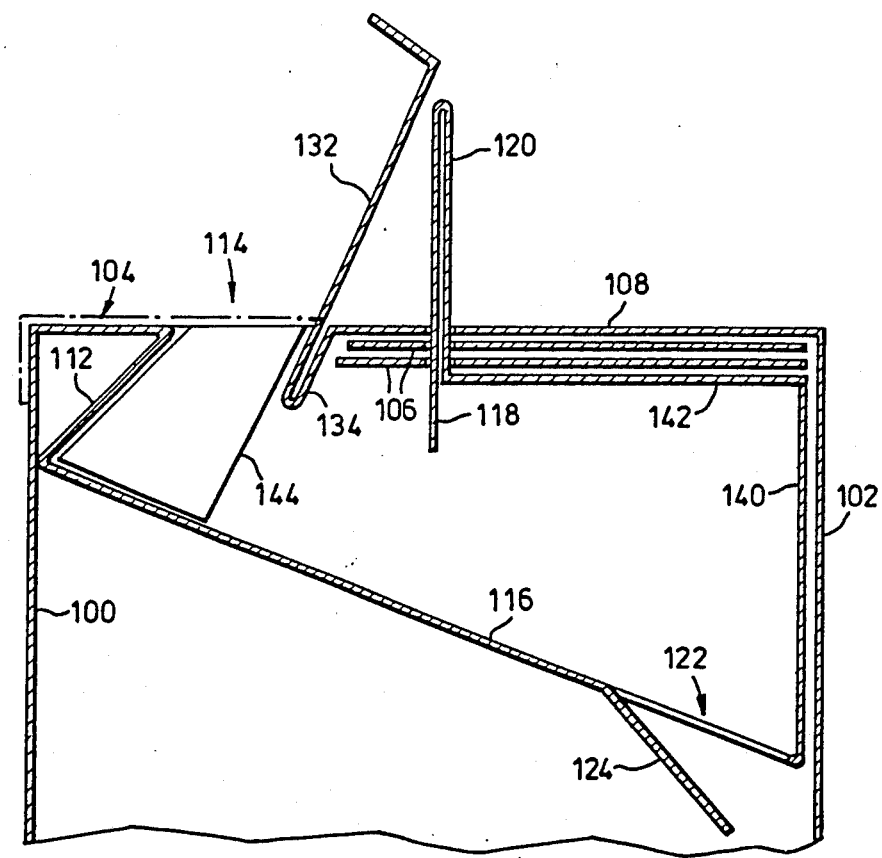
FIG. 4 is a partial cross section through a third embodiment of container, also suitable for fabrication from cardboard.

Referring now to FIGS. 3-5, the use of cardboard containers may be acceptable in some applications, when using a board selected for puncture resistance, and a plastic film liner (not shown) to provide leak proofing. FIGS. 3 and 4 are sectional details illustrating how such containers may be provided with entrance valving arrangements which allow safe and easy insertion of syringes and other material, yet are highly resistant to hand insertion and unintended spillage of materials.

FIG. 3 shows a section through the top flaps of an erected rectangular cardboard carton. Portions of front and rear walls 100 and 102 and front, side and rear top flaps 104, 106 and 108 can be seen in the drawing, all forming part of a single blank of fluteboard, which except for the front and rear flap portions is similar to the blank shown in FIG. 5, which is the blank utilized to form the embodiment of FIG. 5, and is described in more detail below.

The front flap 104 has a series of folds following a narrow initial horizontal portion 110. A portion 112 is inclined forwardly beneath the portion 110 to form a rigid triangular section beam across the top front of the container, which reinforces the front edge of an opening 114 extending the full width of the container and wide enough to accommodate the largest syringe to be received. The width of the container is similarly selected. The next portion 116 of flap forms the front wall of a chute extending downwardly and rearwardly into the interior of the container for about half the width of the container before reaching a portion 118 folded upon itself, and extending vertically upwards through slots in the flaps 106 and 108 to form a carrying handle 120. The carrying handle 120 is slotted to provide a hand grip and provided with notches at its side to interlock with the slots (a similar arrangement is shown in FIG. 5 described below). A slot 122 is cut through the bottom of portion 118 of a height and width to accommodate the largest item to be received, whilst leaving sufficient material at its edges to support the front wall 116 of the chute. A flap 124 is loosely hinged to the top of this slot so as normally to close it, whilst nevertheless allowing easy passage to articles dropped down the chute. A second flap 126 is suspended from the opposite end of the portion 118, and cooperates with the flap 124 and provides controlled passage of articles from the chute into the interior of the container. Either one of the two flaps may be omitted, but the use of both flaps is found to provide better performance.

The main portions of the flaps 106 and 108 terminate rearwardly of the slot 114, but the flap 108 has a further portion 128 extending downwardly from a hinge fold 130 at the front edge of the main portion of flap 108. This further portion is then folded back upon and secured to itself so as to provide a flap 132 projecting upwardly through the opening 114. The flap 132 serves two purposes; firstly, it forms a lever by means of which the wall 134 formed by the portion 128 and its own lower portion may be swung to and fro within the chute formed between the portions 116 and 118 of the front flap, between a normal position shown in solid lines and the position shown in broken lines. A syringe may be dropped into the hopper formed between the portions 112 and 116 and the wall 134, and then released into the interior of the container by swinging the upper part of portion 128 forwardly. When the container is to be removed for disposal, the upper part of portion 128 may be forced further forwardly to a horizontal position as shown in broken lines, to form a closure lid which may be secured in place for example by a loop 135 on a flap 136 hooked onto a stud 138.

As an alternative, the wall 134 may be made shorter so as to permit passage of a syringe beneath it in its normal position, in which it is locked by interengagement with forward portions of the side flaps 106. The hinge 130 is replaced by a hinge in the portion 128 at the level at which it emerges from the opening 114. This arrangement provides a somewhat less effective labyrinth for preventing hand access, and thus if such an arrangement is used, it is preferred to modify the structure as shown in FIG. 3 so as to lengthen the chute as far as possible within the dimensional limitations of the container.

In FIG. 4, the reference numerals used are as far as practicable the same as those utilized in FIG. 3, and the structures are similar except for the differences described. The portion 116 is extended to reach to the rear wall 102 of the container, and the opening 122 is moved to the rear of this portion, the flap 124 being suspended from the front edge of the openings 122. Portions 140 and 142 of the front flap connecting the portion 116 to the handle 120. The wall 134 is shortened as discussed above, and locked in position between the front edges of the flaps 106 and additional forward portion 144 of these flaps which are folded into the opening 114. This arrangement provides a more extensive and tortuous labyrinth to deter hand access, whilst the discharge of syringes and other items from the chute into the body of the container is controlled by the wall 140 which substantially arrests and aligns the items before allowing them to drop into the container body.

FIG. 5 shows a blank which can be erected into the container of FIG. 4. Since the same reference numerals are utilized, the correspondency between the parts in the figures will be apparent. Additional features to be noted are the cooperation of bottom flaps 146, 148, 150 and 152 which interlock to provide a bottom of the container which has a minimum thickness of two layers throughout, with the flap 148 providing a continuous inner floor to the base of the erected carton. This construction is similar to that utilized in ice-cream cartons to provide a leak resistant base. A flange 158 is provided on one vertical edge of the wall 102 which is connected to the side wall 154 to complete the blank. The notches 160 in the portion of the top front flap which form the handle should be noted. These are dimensioned to interlock with the ends of the slots in the flaps 106 and 108 and prevent upward movement of the flap 108 in the assembled carton, thus holding down the flap 108 and preventing upward displacement of the wall 134. Since the handle is formed by part of the front flap 104 and is supported by the other three top flaps 106 and 108, it can be made very strong, and locks the container rigidly together, thus assisting in safe handling of the container after use.

We claim:

1. A container for disposable syringes comprising a body structure defining an interior chamber and a laterally elongated upper opening in an upward and forward surface of the container, the opening having a length and width sufficient to accept expended medical syringes of commonly used sizes broadside on, an upwardly opening lid for covering the opening and connected by a hinge to the rear of the elongated opening for movement upward and away from the opening, a laterally elongated chute extending into the body structure and having a front wall extending downwardly and rearwardly from the opening to a lower opening into the chamber, a wall extending downwardly from the hinge of the lid into the chute to form within the chute and beneath the lid a labyrinth sufficiently restricted and tortuous to arrest passage of a human hand through a chute short of the lower opening of the latter, and a movable flap supported transversely in the lower opening of the chute for movement into the interior chamber, whereby to control passage to the rear of the lower end of the front wall of the chute, into the interior chamber, of a syringe dropped down the chute.

2. A container according to claim 1, wherein the wall extending downwardly from the hinge is coupled with the lid for movement therewith into a position closing the chute as the lid is moved between closed and opened positions.

3. A container according to claim 2, wherein the flap forming is a downward extension of the wall extending downwardly from the hinge.

4. A container according to claim 1, wherein the wall extending downwardly from the hinge is fixed.

5. A container according to claim 1, wherein the lower opening into the interior chamber is defined in the front wall of the chute at its bottom end, and a rear wall of the chute adjacent the rear wall of the interior chamber is located to arrest rearward movement of material dropped down the chute, said rear wall of the chute cooperating with the flap to control passage of material from the chute into the interior chamber.

6. A container according to claim 1, wherein the lower opening into the interior chamber is formed by an aperture in a vertically extending rear wall of the chute, and the flap to control passage of material from the chute to the interior chamber is suspended in said aperture.

7. A container according to claim 3, wherein the lid further includes an actuating lever extending rearwardly of the hinge and externally of the container, whereby the lid and the wall extending downwardly from the hinge may be moved between their respective positions.

8. A container according to claim 7, further including a handle pivotally hinged thereto for movement between a vertical carrying position and a rearwardly directed folded position in which it rests upon and forms an extension of the actuating lever.

9. A container according to claim 7, wherein the lid and at least the upper portion of the structure defining the chute are formed as a superstructure mounted on a lower body structure defining the interior chamber.

10. A container according to claim 9, wherein the lower body structure is a rectangular tinplate container.

11. A container according to claim 1, erected from a cardboard blank.

12. A container according to claim 11, wherein a front edge of the laterally elongated opening is formed by successive portions of a top front flap of the blank folded to form a hollow beam, the front and rear walls of the chute are formed by further portions of the top front flap, and a carrying handle for the container is formed by further portions of the top front flap, locked into an aperture in a top rear flap to prevent lifting of the portions of the latter which form said wall extending downwardly from the hinge.

13. A container according to claim 1, wherein the flap is supported to permit movement independent of the lid.

* * * * *